United States Patent [19]

Yasui et al.

[11] Patent Number: 5,192,685
[45] Date of Patent: Mar. 9, 1993

[54] BIFIDOBACTERIUM STRAINS HAVING HIGH IGA INDUCTION POTENTIAL

[75] Inventors: Hisako Yasui; Kazuhito Hayakawa; Makoto Ohwaki; Tatsuhiko Kan, all of Tokyo, Japan

[73] Assignee: Kabushiki Kaisha Yakult Honsha, Tokyo, Japan

[21] Appl. No.: 512,131

[22] Filed: Apr. 20, 1990

[30] Foreign Application Priority Data

Apr. 21, 1989 [JP] Japan .................................. 1-100282

[51] Int. Cl.$^5$ .............................................. C12Q 1/00
[52] U.S. Cl. ...................................... 435/252.1; 435/4
[58] Field of Search ................................ 435/252.1, 4

[56] References Cited

U.S. PATENT DOCUMENTS

| 4,435,432 | 3/1984 | Klupsch | 435/822 |
| 4,645,667 | 2/1987 | Hashimoto et al. | 424/195.1 |
| 4,797,389 | 1/1989 | Nakaya et al. | 514/54 |

FOREIGN PATENT DOCUMENTS 0135883 8/1984 Japan.

Primary Examiner—Douglas W. Robinson
Assistant Examiner—Deborah K. Ware
Attorney, Agent, or Firm—Michael N. Meller

[57] ABSTRACT

The present invention is to provide an easy, rapid method for screening a great amount of substances having IgA induction potential. The IgA induction potential herein mentioned means the potential to activate and enhance the activity of IgA production cells to produce secretory-type IgA in response to antigen. The present invention is to provide bacterial strains of genus Bifidobacterium obtained by the method for screening substances having IgA induction potential. More specifically, the present invention is to provide *Bifidobacterium longum* YIT 4062, *Bifidobacterium breve* YIT 4063 and *Bifidobacterium breve* YIT 4064. The three strains obtained by the present invention have high IgA induction potential.

4 Claims, No Drawings

BIFIDOBACTERIUM STRAINS HAVING HIGH IGA INDUCTION POTENTIAL

BACKGROUND OF THE INVENTION

1. Field of the Invention

The present invention relates to a method capable of easy screening of a substance having production potential of secretory-type IgA (so called IgA induction potential) which inhibits the binding of microorganisms and allergens to tunica mucosa.

The present invention also relates to a bacterial strain of genus Bifidobacterium, which is screened by the method and which exhibits strong IgA induction potential.

2. Description of the Prior Art

Immunoglobulin, being antibody or protein having a structural and functional relation with antibody, is classified in terms of functional and structural properties into five different classes i.e. IgG, IgM, IgA, IgD and IgE.

IgA among them comprises two subclasses i.e. IgA1 and IgA2. In IgA1, the L chain (light chain) is covalently bonded with the H chain (heavy chain) thereof, while in IgA2 the L chain is bound in S—S bond with each other instead of binding to the H chain. As for the composition ratio regarding IgA1 and IgA2, IgA1 reaches 90% of total serum IgA, and IgA2 reaches 60% of total secretory-type IgA.

The production sites of IgA exists in submucosal plasma cells such as gut-tunica propria and the like, sialaden and mammary gland. In human gut-tunica propria, the number of IgA production cells is far greater than that of IgG production cells and the ratio between them is about 20:1 in remarkable contrast of the ratio of 1:3 (IgA:IgG) in lympho nodes and spleen. IgA in secreted mucus is formed in dimer having a J-chain component and has a secretory component attached thereto which can be observed only in small amount in serum IgA. This component is attached to a dimeric IgA molecule while it is secreted from plasma cells beneath the tunica mucosa of gut and airway into mucus.

Secretory-type IgA in secreted mucus inhibits the binding of highly pathogenic microorganisms and allergens to tunica mucosa. Thus, secretory-type IgA binds food components functioning as allergens to inhibit the absorption thereof through gastric wall, in addition to prevention of infection of pathogenic microorganisms.

The preventive mechanism of antibody is now illustrated in the following inhibitive mechanism of absorption through gastric wall. Antibody directly binds to the surface of microorganisms in order to prevent infection of exotoxin secreted from pathogenic microorganisms. That is, the antibody may directly bind to the microorganisms to exert a variety of effects.

Alternatively, there has been also observed some substances having the potential to process antigen effectively after nonspecific stimulation of antibody production cells, and such property is often called built-in-adjuvanticity.

It is known, for example, that cholera toxin to be produced by *Vibrio cholerae*, a causative toxin for diarrhea, may affect tunica mucosa intestini tenuis to modify ionic permeability thereof, so that the toxin may induce intestinum tenuis to discharge a great amount of water and electrolytes to lead to the occurrence of diarrhea. It is also known that the cholera toxin B subunit obtained by detoxifying the principle component of the toxin exhibits immunological response such that it permeates into tunica mucosa to facilitate the production of IgA antibody (so-called IgA induction potential), namely, the cholera toxin B subunit functions as adjuvant.

Ninety-nine percent of enterobacterium flora in breast-feeding babies within several weeks after birth is occupied by bacterial strains of genus Bifidobacterium as an enterobacterium which cannot exert any pathogenicity to humans and animals. The above fact has indicated that the bacterial strains may have certain roles in biophylaxis.

*Bifidobacterium longum*, one of the genus Bifidobacterium, is known to increase total IgA in feces if administered orally.

However, the induction potential of secretory-type IgA has not been comparatively studied yet and an easy method for the investigation therefor has never been established, either.

It has not been completely elucidated yet how effective the enterobacterium may be. It has not been identified specifically whether there may be any difference in IgA induction potential among a variety of bacterial strains of genus Bifidobacterium known not to have any pathogenicity to humans and animals.

SUMMARY OF THE INVENTION

The objective of the present invention is to establish an easy method using IgA production cells for screening substances having IgA induction potential. Another objective of the present invention is to define any difference in IgA induction potential among bacterial strains of genus Bifidobacterium to screen a strain having strong IgA induction potential. The present invention may clearly identify the difference in IgA induction potential among the bacterial strains and realize the screening of a strain having strong IgA induction potential.

Regarding the first invention, the method for screening substances having IgA induction potential, comprises culturing aseptically cells of Peyer's patch as one of the gut-associated lymphoid tissue containing a great amount of IgA production cells, adding the solution of a subjective substance or a suspension thereof to the culture medium for culture for a given period, measuring IgA secreted from the IgA production cells in the culture medium after culturing for a given period, and selecting a substance having IgA induction potential based on a ratio of the produced IgA in a group with addition of a subjective substance to that in a group without the substance.

Regarding to the second invention, the bacterial strain of genus Bifidobacterium having IgA induction potential, is one obtained by the method for screening substances having IgA induction potential according to the first invention described above.

In accordance with the first invention, a substance having IgA induction potential may be screened, based on a ratio of the IgA produced in a group with addition of a subjective substance to that in a group without the subjective substance after aseptically culturing cells containing a great amount of IgA production cells. The screening procedure is easy to perform, and may further accomplish, for a short period, screening for a great number of kinds of substances having IgA induction potential.

Furthermore, the bacterial strain according to the second invention is one of genus Bifidobacterium obtained by using the screening method for substances having IgA induction potential according to the first invention. Accordingly, the IgA induction potential of genus Bifidobacterium which is known not to show any pathogenicity to humans and animals, exerts an adjuvant activity i.e. an ability to stimulate non-specifically antibody production cells to process antigen more effectively, together with the initial IgA induction potential due to foreign body cognition (the antigenicity of the bacterial strain).

The bacterial strain of genus Bifidobacterium having IgA induction potential, obtained by the present invention, has an action to activate and enhance the activity of the IgA production cells to produce secretory-type IgA in response to antigen. More particularly, the present invention discloses three bacterial strains of genus Bifidobacterium, YIT4062, YIT4063 and YIT4064.

Each of the bacterial strains, YIT4062, YIT4063 and YIT4064, has outstandingly stronger IgA induction potential, compared with the known bacterial strains of genus Bifidobacterium deposited in public organizations; the ratio of the IgA produced by the group with addition of a subjective substance to that by the group without the substance (namely, the increment) is 12 or more. Each strain may stimulate the potential of IgA production cells strongly.

The bacterial strains, YIT4062, YIT4063 and YIT4064, have been already deposited in the Agency of Industrial Science and Technology, Fermentation Research Institute as FERM BP-2822, FERM BP-2823 and FERM BP-2824, respectively.

In accordance with the first invention, a substance having IgA induction potential may be screened, based on a ratio of the IgA produced in a group with addition of a subjective substance to that in a group without the substance after aseptically culturing cells containing a great amount of IgA production cells of Peyer's patch. The screening procedure is easy to perform, and may further accomplish rapid screening for a great number of kinds of substances having IgA induction potential.

Furthermore, the bacterial strain according to the second invention is one of genus Bifidobacterium obtained by using the screening method for substances having IgA induction potential according to the first invention. Accordingly, the IgA induction potential of genus Bifidobacterium which is known not to show any pathogenicity to humans and animals, exhibits an adjuvant activity i.e. an ability to stimulate non-specifically antibody production cells to process antigen more effectively, together with the initial IgA induction potential due to foreign body cognition (the antigenicity of the bacterial strain).

The bacterial strain of genus Bifidobacterium having IgA induction potential, obtained by the present invention, has an action to activate and enhance the activity of the IgA production cells to produce secretory-type IgA in response to antigen.

For the reasons described above, such strain may be widely used as nutrient agents and mixing compositions for so-called healthy foods and functional foods, besides prophylactic agents for enteral infection and incidence of allergy.

DESCRIPTION OF THE PREFERRED EMBODIMENTS

The present invention is to provide the finding that the three bacterial strains originating from 120 Bifidobacterium strains isolated from feces of newborn babies, babies, infants, adults and elderly, induce IgA production activity of Peyer's patch cells more strongly than the known Bifidobacterium strains.

The known bacteria now used are those described on the catalogs of the American Type Culture Collection (ATCC) and the Japan Collection of Microorganisms (JCM).

The screening procedure of the bacterial strains of genus Bifidobacterium, having strong IgA induction potential, according to the present invention, is now explained in examples.

The identification technique of the bacterial strains used in experiments, and the preparation and experimental methods therefor are as follows;

1) The identification of isolated bacteria

Bacteria isolated are identified according to the sugar-fermentation test (see Anaerobe Laboratory Manual, 4th ed., ed. by L. V. Holdeman et. al. 1977).

2) The preparation of bacteria

Each Bifidobacterium strain isolated from feces of newborn babies, babies, infants, adults and elderly, in total 120 strains, is inoculated on the GAM medium and cultured under anaerobic condition at 37° C. for 48 hours. These bacteria are washed in phosphate buffer two times and subjected to heating at 100° C. for 30 min for use.

3) Isolation of Peyer's patch cells

Peyer's patch is aseptically taken out from mouse intestine and placed in a solution of Dispase (1.5 mg Dispase/ml Joklik-modified MEM), and then stirred at 37° C. for 30 to 40 minutes to recover single cells separated into the solution. Such procedure is repeated 4 or 5 times before centrifuge and washing, to obtain Peyer's patch.

EXAMPLE 1

The isolated Bifidobacterium strains (120 strains) obtained after repeating three times the procedures for separation into single colonies, were examined of their IgA induction potential. IgA production was determined as follows;

Cells of Peyer's patch ($5 \times 10^5$) and each of a variety of bacterial strains in suspension at a concentration of $OD_{660}=0.275$ were placed in each well of a 96-well microtiter plate and cultured under 5% $CO_2$/air at 37° C. in the Eagle medium containing 5% fetal calf serum [Eagle MEM (manufactured by Nissui Pharmaceuticals, Co.Ltd) 9.4 g/l, 200 mM glutamine 10 ml/l (2 mM), MEM nonessential amino acid ($\times 100$GIBCO) 10 ml/l, 100 mM sodium pyruvate (manufactured by Sigma, Co. Ltd.) 10 ml/l (1 mM), pH7.2, adjusted with 1N NaOH].

During the culture, there was continued every day the division per well of 0.02 ml of the nutrient mixture [MEM essential amino acid ($\times 50$GIBCO) 5 ml, MEM nonessential amino acid ($\times 100$GIBCO) 2.5 ml, 200 mM glutamine 2.5 ml, Dextrose 500 mg, Eagle MEM (—$NaHCO_3$) (manufactured by Nissui Pharmaceuticals, Co. Ltd) 35 ml, adjusted at pH 7.2 with 1N NaOH before addition of 7.5 ml of 7.5% $NaHCO_3$]. IgA secreted into the supernatant of the culture medium was measured by ELISA (enzyme-linked immunosorbent assay) over time for 7 days.

ELISA was carried out as follows. As a buffer solution, sodium carbonate buffer (pH 9.6) was used. One hundred microliter of goat anti-mouse IgA (manufactured by Cappel Co. Ltd.) was added to an immunoplate well and was reacted at 4° C. overnight for adsorption. After washing with a washing solution (0.05% Triton X-100, PBS) three times, sodium carbonate buffer containing 1% bovine serum albumin (BSA) was added and reacted at 37° C. for 1.5 hours, in order to cover the unabsorbed part of the well. Again, after washing with the washing solution, 90 microliter of each diluted sample of the supernatant from the culture medium was added to each of 96 wells and left to stand at 37° C. for 1.5 hours. After washing, 100 microliter of peroxidase-bound goat anti-mouse IgA (manufactured by Cappel Co. Ltd.) was added to each well and left to stand at 37° C. for 1.5 hours. After washing again with the washing solution, 100 microliter of a substrate solution, which was produced just before use by adding 10 microliter of aqueous hydrogen peroxide solution to the solution of 20 mg of 0-phenylenediamine dissolved in 50 ml of citrate buffer, pH 7.2, was added and reacted at 37° C. for 10 minutes, immediately followed by addition of 50 microliter of 2.5M sulfate per well, in order to terminate the reaction. The absorbance of each well at $OD_{492}$ nm was measured by using a Titertek Multiscan manufactured by Flow Laboratory Inc.

As standard, mouse IgA (myelona) (manufactured by ICN Immuno-Biological, Co. Ltd.) was used. The value of IgA was represented in the unit microgram/ml supernatant of culture medium.

The increment of IgA was determined by the following formula;

7 kinds of known bacterial strains, as is shown in Table 1.

TABLE 1

| IgA Induction Potential of Isolated Bacterial Strains and Known Strains | | | |
|---|---|---|---|
| Bacterial strains | | IgA (μg/ml) | Increment |
| Isolated bacterial strains | | | |
| | YIT4062 | 3.34 | 12.9 |
| | 4063 | 4.87 | 18.7 |
| | 4064 | 6.89 | 26.5 |
| Known strains | | | |
| B. Breve | YIT4014 (ATCC15700) | 2.90 | 11.2 |
| | YIT4015 (ATCC15698) | 1.64 | 6.3 |
| | YIT4049 (ATCC15701) | 1.58 | 6.1 |
| | YIT4006 | 2.81 | 10.8 |
| B. longum | YIT4021 (ATCC15707) | 0.73 | 2.8 |
| | YIT4037 (ATCC15708) | 0.94 | 3.6 |
| B. animalis | YIT4044 (JCM1190) | 0.65 | 2.5 |
| No addition of bacteria (only cells of Peyer's patch) | | 0.26 | 1.0 |

EXAMPLE 2

The three strains having strong IgA induction potential were identified by the sugar-fermentation test and the DNA homology test. The results of the sugar-fermentation tests are shown in Table 2. YIT 4062 was identified to be *Bifidobacterium longum* (*B. longum*); YIT 4063, 4064 were identified to be *Bifidobacterium breve* (*B. breve*).

TABLE 2

| | Identification Test (Sugar Fermentation Test) | | | | | | |
|---|---|---|---|---|---|---|---|
| | Known strains | | | | Isolated bacterial strains | | |
| Sugar | B. breve ss breve | B. breve ss parvulorum | B. longum | B. animalis | YIT 4064 | YIT 4063 | YIT 4062 |
| Arabinose | − | − | + | + | − | − | + |
| Xylose | − | − | + | + | − | − | + |
| Ribose | + | + | + | + | + | + | + |
| Glucose | + | + | + | + | + | + | + |
| Mannose | + | + | ± | ± | + | + | ± |
| Fructose | + | + | + | + | + | + | + |
| Galactose | + | + | + | + | + | + | + |
| Sucrose | + | + | + | + | + | − | + |
| Maltose | + | + | + | + | + | + | + |
| Cellobiose | + | + | − | − | + | + | − |
| Lactose | + | + | + | + | + | + | + |
| Trehflose | ± | − | − | − | − | − | − |
| Raffinose | + | + | + | + | + | + | + |
| Melezitose | ± | ± | + | − | − | − | + |
| Dextrin | ± | + | ± | ± | + | + | − |
| Starch | ± | + | − | − | − | − | − |
| Glycogen | ± | + | − | − | − | − | − |
| Inulin | − | ± | − | − | − | − | − |
| Mannitol | + | − | − | − | + | − | − |
| Sorbitol | + | − | − | − | + | − | − |
| Inositol | − | − | − | − | − | − | − |
| Esculin | + | + | − | − | + | + | − |
| Salicin | + | + | − | − | + | + | − |
| Amygdalin | + | + | − | − | − | + | − |
| | | | | | B. breve | B. breve | B. longum |

$$\text{Increment} = \frac{\text{IgA (microgram/ml) in supernatant of the culture medium of Peyer's patch cells with bacteria added}}{\text{IgA (microgram/ml) in supernatant of the culture medium of Peyer's patch with no bacteria added}}$$

As a result, there could be detected three bacterial strains (YIT 4062, 4063 and 4064) having stronger IgA induction potential (index value of 12 or more) than the As is described above, the fact that the three bacterial strains according to the present invention were identified as *Bifidobacterium longum* or *Bifidobacteirum breve* (H. Yasui, A. Mike and M. Ohwaki, 1989. J. Dairy Sci. 72:30–35) and that the strains are capable of enhancing IgA production potential of the cells of Peyer's patch indicates that the strains may act as adjuvant.

As has been described above, the first invention may provide an easy, rapid method for screening a great amount of substances having IgA induction potential. The method may be used in near future for screening other substances or bacterial strains, having strong IgA induction potential, other than the three strains.

Due to the fact that the Bifidobacterium strains of the second invention, detected by the present first invention, have been known not to show any pathogenicity for humans and animals, the IgA induction potential thereof may be considered to be the one as adjuvant actions, not as antigenicity as foreign bodies of themselves.

The above experiments were carried out using the thermally killed three bacterial strains of the present invention. They proposed the evidence that the strains are capable of enhancing IgA production potential of the cells of Peyer's patch. Thus, they indicates that there may exist in the cell walls thereof some substances capable of activating IgA induction potential. Because these indicate that similar effects may be obtained by using live such bacteria, the strains may be prepared in pharmaceuticals in powders, drink or tablets, and may be used as sources for functional foods.

These three strains enhance IgA production potential of the cells of Peyer's patch as a principal tissue in the gastric mucosal immune system. The oral administration thereof may enhance the production potentials of IgA and intraluminally secreting-type IgA of the cells of Peyer's patch. Additionally, the bacterial strains of the present invention may be expected to enhance strongly IgA production in mucosal layers other than Peyer's patch, so that they may be effective against prophylaxis of enteral infection and inhibition of allergy absorption. Furthermore, it may be suggested that they will exhibit satisfactory effects to prevent cold and allergic rhinitis.

These bacteria may be administered orally, but they may not cause any problems on safety. In addition, they may be handled quite easily.

The thermally killed microorganisms may be satisfactorily used as effective components, which provides easy preparation of the microorganisms into pharmaceuticals, and simple storage and use thereof.

The killed bacteria may be thus used in a wide range such as mixing components for nutrient agents, so-called healthy foods and functional foods, besides prophylactic drugs for enteral infection and allergy episodes.

What is claimed is:

1. A biologically pure bacterial strain selected from *Bifidobactierum longum* or *Bifidobacterium breve* having IgA induction potential of 12 or more, which is obtained by the method comprising:
    culturing, aseptically in a culture medium, cells of Peyer's patch containing a great amount of IgA production cells, bacterial strains,
    adding a solution of a substance which has IgA induction potential to be screened, or a suspension thereof, to the culture medium for culturing for a given period,
    measuring the IgA secreted from the IgA production cells in the culture medium after culturing for a given period, and
    isolating said strain having IgA induction potential, of 12 or more based on a ratio of the produced IgA in a group containing said bacterial strain to that in a group without said bacterial strain,
    said bacterial strain being that of *Bifidobacterium longum* (*B. longum*) or *Bifidobacterium breve* (*B. breve*).

2. A bacterial strain of genus Bifidobacterium having IgA induction potential according to claim 1 wherein the bacterial strain is *Bifidobacterium longum* YIT 4062.

3. A bacterial strain of genus Bifidobacterium having IgA induction potential according to claim 1 wherein the bacterial strain is *Bifidobacterium breve* YIT 4063.

4. A bacterial strain of genus Bifidobacterium having IgA induction potential according to claim 1 wherein the bacterial strain is *Bifidobacterium breve* YIT 4064.

* * * * *